United States Patent
Heid

(10) Patent No.: US 8,903,471 B2
(45) Date of Patent: Dec. 2, 2014

(54) BEAM DEFLECTION ARRANGEMENT WITHIN A COMBINED RADIATION THERAPY AND MAGNETIC RESONANCE UNIT

(75) Inventor: Oliver Heid, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/878,893

(22) PCT Filed: Jun. 13, 2011

(86) PCT No.: PCT/GB2011/051093
§ 371 (c)(1),
(2), (4) Date: Apr. 11, 2013

(87) PCT Pub. No.: WO2012/049466
PCT Pub. Date: Apr. 19, 2012

(65) Prior Publication Data
US 2013/0197351 A1 Aug. 1, 2013

(30) Foreign Application Priority Data
Oct. 15, 2010 (GB) .................................. 1017436.5

(51) Int. Cl.
| | |
|---|---|
| *A61B 6/00* | (2006.01) |
| *A61N 5/10* | (2006.01) |
| *G01R 33/48* | (2006.01) |
| *G21K 1/093* | (2006.01) |

(52) U.S. Cl.
CPC ............ *A61N 5/1039* (2013.01); *A61N 5/1049* (2013.01); *A61N 5/1043* (2013.01); *G01R 33/4808* (2013.01); *A61N 2005/1055* (2013.01); *G21K 1/093* (2013.01)

USPC .............................................. 600/411; 378/65

(58) Field of Classification Search
USPC ................................. 600/411; 378/65, 68, 69
See application file for complete search history.

(56) References Cited

U.S. PATENT DOCUMENTS

| | | | |
|---|---|---|---|
| 6,366,798 | B2 | 4/2002 | Green |
| 6,925,319 | B2 | 8/2005 | McKinnon |
| 2005/0197564 | A1 | 9/2005 | Dempsey |
| 2006/0273795 | A1 | 12/2006 | Rieke et al. |
| 2008/0208036 | A1 | 8/2008 | Amies et al. |

FOREIGN PATENT DOCUMENTS

| | | |
|---|---|---|
| GB | 2247478 A | 3/1992 |
| GB | 2393373 A | 3/2004 |
| GB | 2427479 A | 12/2006 |
| WO | 2004/024235 | 3/2004 |

*Primary Examiner* — Unsu Jung
*Assistant Examiner* — Phong K Huynh
(74) *Attorney, Agent, or Firm* — Schiff Hardin LLP

(57) ABSTRACT

In a radiation therapy and magnetic resonance unit, a magnetic resonance diagnosis part is provided. A radiation therapy part is provided for irradiation of an irradiation area within an interior of the diagnosis part. The radiation therapy part comprises a beam deflection enclosure for deflecting an electron beam toward an axis of the diagnosis part from an initial trajectory parallel to the axis. The beam deflection enclosure comprises a first magnetic field in a region of the beam deflection enclosure but of opposite direction and effective to cancel a main magnet field of the diagnosis part. A second magnet field is directed perpendicular to a trajectory of the electron beam to cause the electron beam to be deflected inward towards the axis.

10 Claims, 4 Drawing Sheets

BEAM DEFLECTION ARRANGEMENT WITHIN A COMBINED RADIATION THERAPY AND MAGNETIC RESONANCE UNIT

BACKGROUND

The disclosure relates to an improved beam deflection arrangement within a combined radiation therapy and magnetic resonance unit.

Generally in radiation therapy the aim is to irradiate a target within the human body in order to combat diseases, in particular cancer. For this purpose a high dose of radiation is specifically generated in an irradiation center (isocentre) of an irradiation apparatus. During irradiation the problem often arises that the irradiation target in the body can move. For instance, a tumor in the abdomen can move during breathing. On the other hand, in the period between radiation treatment planning and actual radiation treatment a tumor may have grown or have already shrunk. It was therefore proposed to check the position of the irradiation target in the body during radiation treatment by imaging, in order to control the beam or if necessary discontinue the irradiation, and thus increase the success of the therapy. This is in particular relevant for irradiation targets in the upper and lower abdomen as well as in the pelvic area, for example the prostate. To minimize the dose of radiation outside the target volume and thus protect healthy tissue, the entire radiation generation is moved around the patient. This concentrates the radiation dose in the beam in the area of the rotational axis.

Both X-ray and ultrasound systems were proposed as the imaging medium for monitoring the therapy. These, however, provide only a limited solution to the problem. In the case of ultrasound imaging the necessary penetration depth is lacking for many applications. In X-ray imaging the X-ray sensors can be disrupted or damaged by the gamma radiation of the accelerator. Furthermore, the quality of the tissue images is often unsatisfactory.

For this reason, at present mainly positioning aids and fixing devices or markings made on the skin of the patient are used to ensure that the patient is in the same position in the irradiation apparatus as decided in the radiation treatment planning and that the irradiation center of the irradiation apparatus is actually consistent with the irradiation target. These positioning aids and fixing devices are, however, expensive and in most cases they are uncomfortable for the patient. In addition, they conceal the risk of irradiation errors because as a rule no further check of the actual position of the irradiation center is carried out during irradiation.

Magnetic resonance is a known technique which permits both particularly good soft-tissue imaging as well as spectroscopic analysis of the area being examined. As a result this technique is fundamentally suitable for monitoring radiation therapy.

In U.S. Pat. No. 6,366,798 a radiation therapy device is combined with various magnetic resonance imaging systems. In all the different versions mentioned here the magnet arrangement of the magnetic resonance imaging system is divided into two parts. In addition, in some versions key parts of the magnetic resonance imaging system rotate with the radiation source of the radiation therapy device. In each case the radiation source is outside the magnetic resonance imaging system and must be protected by means of shields from the stray field of the magnetic resonance imaging system. A division of the magnet, a rotatable magnet and shielding of the radiation source represent elaborate technical solutions and increase the cost.

In GB 2 427 479 A, U.S. Pat. No. 6,925,319 B2, GB 2 247 478 A, US 2005/0197564 A1 and US 2006/0273795 A1 further devices are described in which a radiation therapy device or an X-ray imaging system are combined with a magnetic resonance imaging system.

GB 2 393 373 A describes a linear accelerator with an integrated magnetic resonance imaging system. In one exemplary embodiment the magnetic resonance imaging system comprises means for compensation of a magnetic field in order to minimize the field strength of the magnetic field of the magnetic resonance imaging system at the location of the accelerator. In another exemplary embodiment a filter is used in order to compensate for possible heterogeneity caused in a therapy beam by the magnetic field of the magnetic resonance imaging system.

US2008/0208036 describes a combined radiation therapy and magnetic resonance unit similar to that described below in relation to FIGS. 1-4 of the present application.

FIG. 1 shows a schematic representation (not to scale) of a conventional combined radiation therapy and magnetic resonance unit 1 as described in US2008/0208036 with a magnetic resonance diagnosis part 3 and a radiation therapy part 5. The magnetic resonance diagnosis part 3 comprises a main magnet 10, a gradient coil system comprising two, in this case, symmetrical partial gradient coils 21A, 21B, high-frequency coils 14, for example two parts of a body coil 14A, 14B, and a patient bed 6. All these components of the magnetic resonance part are connected to a control unit 31 and an operating and display console 32.

In the example presented, both the main magnet 10 and the partial gradient coils 21A, 21B are essentially shaped like a hollow cylinder and are arranged coaxially around the horizontal axis 15. The inner shell of the main magnet 10 limits in radial direction (facing away vertically from the axis 15) a cylinder-shaped interior 7, in which the radiation therapy part 5, the gradient system, high-frequency coils 14 and the patient bed 6 are arranged. More precisely the radiation therapy part 5 is located in the interior 7 between the outer side of the gradient coil system 21A and 21B and the inwardly facing shell surface of the main magnet 10.

In addition to the magnet coils the main magnet 10 comprises further structural elements, such as supports, housing etc., and generates the homogenous main magnetic field necessary for the magnetic resonance examination. In the example shown the direction of the main magnetic field is parallel to the horizontal axis 15. High-frequency excitation pulses which are irradiated by means of high-frequency coils 14 are used to excite the nuclear spins of the patient. The signals emitted by the excited nuclear spins are also received by high-frequency coils 14.

The axially distanced partial gradient coils 21A, 21B in each case comprise gradient coils 20, which are in each case completely enclosed by a shield 27. The gradient coil 20 comprises supports and individual gradient coils which irradiate magnetic gradient fields for selective layer excitation and for location-coding of the magnetic resonance signals in three spatial directions.

The radiation therapy part 5 is arranged on a gantry 8 and comprises an electron accelerator 9, which here is configured as a linear accelerator, a beam deflection arrangement 17, a target anode 19, a homogenizing body 22 and a collimator 23. The gantry 8 can feature a recess (broken lines), by which access to the magnetic resonance diagnosis part remains possible also from this side.

The electron accelerator 9 of the radiation therapy part 5 comprises an electron source 11, for example a tungsten cathode, which generates an electron beam 13, which is accelerated by the electron accelerator 9 preferably pulsed parallel to the main magnetic field of the main magnet 10. The electron accelerator 9 for example generates electron beam pulses with a length of 5☐s every 5 ms. If the electron accelerator 9 generates pulsed electron beams 13, it can be built more compactly, e.g. with a length of about half a meter, and still withstand the impact of the high-energy electron beams 13.

The electrons of the electron beam 13 are accelerated by electric alternating fields in cylinder-shaped hollow conductors of the electron accelerator 9. The electrons of the electron beam 13 are accelerated to energies up to a magnitude of several MeV. The electron accelerator 9 is connected to an accelerator control unit 12 to control the alternating fields and the electron source 11.

The electron beam 13 leaves the electron accelerator 9 at the end opposite the electron source and is deflected by the beam deflection arrangement 17 through 90° radially inward in the direction of axis 15. For this purpose the beam deflection arrangement 17 comprises a magnet which generates a suitable magnetic field. The magnet is configured as an electromagnet made of non-ferromagnetic materials to prevent undesired interaction with the surrounding magnetic fields. As the beam deflection arrangement 17 has to work in a strong, outer magnetic field, it has been modified compared with other conventional beam deflection arrangements.

To be able to deflect the pulsed electron beam 13 in a small space, the beam deflection arrangement 17 must generate strong magnetic fields. To reduce the power loss, the magnetic field of the beam deflection arrangement 17 is a pulsed magnetic field which is synchronized with the pulsed electron beam 13. For this purpose the beam deflection arrangement 17 is connected to a beam deflection control unit 18 which is also connected to the accelerator control unit 12.

The deflected electron beam 13 hits the target anode 19 and generates an X-ray beam that emerges from the target anode in the beam elongation along an X-ray beam path. The X-ray beam is homogenized by the homogenizing body 22.

The collimator 23 is arranged in an annular slot between the distanced partial gradient coils 21A, 21B in the X-ray beam after the target anode 19. The proximity to the irradiation target thus achieved improves the radiation luminance and the effectiveness of the collimator 23.

The collimator 23 enables the direction of the X-ray beam and the cross-section of the X-ray beam to be influenced. For this purpose the collimator 23 incorporates moveable adjusters 24, which permit the X-ray beam to pass only in a certain direction, e.g. only parallel to the radial axis 26 or up to at most in one direction through an angle α away from the axis 26, and only with a certain cross-section. It is also possible to set the adjusters 24 of the collimator 23 in such a way that no X-ray beams can pass parallel to the axis 26 and only angled X-ray beams in one direction through certain angles away from the axis 26 can pass through. To control the adjusters 24 the collimator 23 is connected to a collimator control unit 25. Such collimators are adequately known. By way of example reference can be made to multi-leaf collimators. They make it possible to perform intensity modulated radiation therapy (IMRT), in which the size, shape and intensity of the X-ray beam can be optimally adapted to the irradiation target. In particular IMRT also enables the irradiation center to be positioned outside the rotational axis of the radiation therapy device.

The X-ray beam penetrates the examination subject, in this case the patient P, and the X-ray beam path runs through a diagnosis volume D of the magnetic resonance diagnosis part 3. To minimize the local dose of radiation outside the irradiation target volume, the radiation therapy part rotates around the axis 15 of the main magnetic field. As a result, the full dose is applied only in the irradiation center B. The collimator 23 constantly adapts the cross-section of the X-ray beam to the actual outline of the irradiation target even during rotation. The gantry 8 is configured for rotation of the radiation therapy part. A gantry control unit 29 controls the movement of the radiation therapy part 5. As an example the radiation therapy part 5 is shown as radiation therapy part 5' after rotation through 180°.

The gantry control unit 29, the collimator control unit 25, the beam deflection control unit 18, the accelerator control unit 12 and the control unit 31 are connected to each other so that the diagnosis data collected by the magnetic resonance diagnosis part, for example the three-dimensional shape of the irradiation target, the rotational position of the radiation therapy part, as well as the collimator settings with regard to cross-section and direction of the X-ray beam and the generation of pulsed beams described above can be coordinated with each other.

The patient bed 6 is preferably moveable in three spatial directions so that the target area of the irradiation can be positioned precisely in the irradiation center B. For this purpose the control unit 32 is expediently configured for controlling a movement of the patient bed.

FIGS. 2 to 4 show segments of further exemplary conventional configurations of a combined radiation therapy and magnetic resonance unit as described in US2008/0208036 which may be improved by inclusion of a beam deflection arrangement. In the exemplary configurations shown in particular the arrangement of a respective radiation therapy part 5, 105, 205, 305 varies from the exemplary embodiment in FIG. 1. For the sake of clarity, therefore, only the upper section of a main magnet 110, 210, 310 of the combined radiation therapy and magnetic resonance unit up to about one high-frequency coil 114, 214, 314 of the combined radiation therapy and magnetic resonance unit is shown. The rest of the configuration and its mode of operation are, unless otherwise described, essentially the same as in the example shown in FIG. 1, to which reference is hereby made.

FIG. 2 shows a main magnet 110 of the combined radiation therapy and magnetic resonance unit on whose side facing an interior 107 of the combined radiation therapy and magnetic resonance unit a gradient coil system 120 is arranged. The gradient coil system 120 comprises in particular primary coils 121 and secondary coils 122. Between primary coils 121 and secondary coils 122 a free space is located in which the radiation therapy part 105 of the combined radiation therapy and magnetic resonance unit is arranged. Such a distanced arrangement of the primary and secondary coils 121 and 122 increases the efficiency of the gradient coil system 120. In addition, high-frequency coils 114 are arranged on the side of the gradient coil system facing the interior 107.

The gradient coil system 120 or at least the primary coils 121 as shown in the example in FIG. 1 can be divided into two partial gradient coils 121A, 121B and arranged in such a way that at least parts of the radiation therapy part 105 can move in an annular space between the parts in a rotation of the radiation therapy part 105 around the axis of the main magnetic field. In this case the high-frequency coils 114 are also advantageously divided correspondingly into two partial high-frequency coils 114A and 114B.

Alternatively it is conceivable for the gradient coil system 120 to be configured in such a way that together with the radiation therapy part 105 it can rotate around the axis of the main magnetic field. In this case a division of the gradient coil system 120 or of the primary coils is not absolutely appropriate. It suffices to configure the primary coil 121 in such a way that it can let the radiation therapy part 105 penetrate into the interior 107 at one point in order to emit the therapy beams onto an irradiation center B. The same applies to the high-frequency coils 114. It may be necessary here to compensate for the mechanical turning of the gradient coil system 120 by suitable activation of the gradient currents. Such an electric rotation of gradient fields is, however, a usual capability of standard magnetic resonance systems. Nevertheless, high requirements should be imposed on the accuracy and reproducibility of the rotation.

Thanks to its particularly compact design this exemplary embodiment gives the patient an exceptional amount of room in the interior 107. Advantageously, a collimator of the radiation therapy part 105 is incorporated in a particularly flat configuration in the exemplary embodiment shown in FIG. 2 in order to give the patient even more room in the interior 107 of the combined radiation therapy and magnetic resonance unit.

FIG. 3 presents a segment of a further combined radiation therapy and magnetic resonance unit. A gradient coil system 220 is arranged on the side of a main magnet 210 facing an interior 207 of the combined radiation therapy and magnetic resonance unit. Standard components can be used for the main magnet 210 and the gradient system 220, which among other things reduces cost.

Again on the side of the gradient system 220 facing the interior 207 high-frequency coils 214 are arranged. Between the gradient system 220 and the high-frequency coils 214, however, adequate space is left in order to arrange a radiation therapy part 205 of the combined radiation therapy and magnetic resonance unit between the gradient system 220 and the high-frequency coils 214.

During irradiation of an irradiation center B the radiation therapy part 205 rotates around the main magnetic field axis of the combined radiation therapy and magnetic resonance unit. In a similar way as in the structure of FIG. 2 the high-frequency coils 214 can here too either be divided into two partial high-frequency coils 214A and 214B in such a way that at least parts of the radiation therapy part 205 can move in an annular gap between the partial high-frequency coils 214A and 214B. Alternatively, the high-frequency coils 214 can be rotated with the radiation therapy part 205.

FIG. 4 shows schematically a segment of a further combined radiation therapy and magnetic resonance unit. In this case, high-frequency coils 314 are arranged within a gradient system 320 which itself is arranged within a main magnet 310. A radiation therapy part 305 is arranged on the side facing an interior 307 of the combined radiation therapy and magnetic resonance unit. As in the arrangements presented above the radiation therapy part 305 rotates during irradiation around the main magnetic field axis of the combined radiation therapy and magnetic resonance unit. In this exemplary embodiment no particular structural measures are necessary with regard to the gradient system 320 and the high-frequency coils 314 to make this rotational movement of the radiation therapy part possible.

Advantageously the inner radius of the high-frequency coils 314 is as big as possible and the radiation therapy part is as flat as possible so that the patient is not cramped in the interior 307.

The radiation therapy part 105, 205, 305 of the structures in FIGS. 2 to 4 in each case incorporates essentially the same construction as the radiotherapy part 5 shown in FIG. 1. For the sake of clarity the individual components are not shown again. The rotational movement of the radiation therapy parts 105, 205, 305 and/or the gradient coil system 120, 220, 320 and/or the high-frequency coils 114, 214 is indicated in each case by a broken-line arrow.

If necessary, in the structures of FIGS. 2, 3 and 4 the radiation therapy part 105, 205, 305 and the magnetic resonance part, in particular the gradient system 120, 220, 320 and/or the high-frequency coils 114, 214, 314, are not operated at the same time but are alternated in order to exclude possible disruptive interaction, in particular between moving parts of the radiation therapy part 105, 205, 305 and electromagnetic alternating fields of the magnetic resonance part.

SUMMARY

It is an object to provide an improved beam deflection arrangement for a combined radiation therapy and magnetic resonance unit for example as described above.

In a radiation therapy and magnetic resonance unit, a magnetic resonance diagnosis part is provided. A radiation therapy part is provided for irradiation of an irradiation area within an interior of the diagnosis part. The radiation therapy part comprises a beam deflection enclosure for deflecting an electron beam toward an axis of the diagnosis part from an initial trajectory parallel to the axis. The beam deflection enclosure comprises a first magnetic field in a region of the beam deflection enclosure but of opposite direction and effective to cancel a main magnet field of the diagnosis part. A second magnet field is directed perpendicular to a trajectory of the electron beam to cause the electron beam to be deflected inward towards the axis.

Further advantages and details of the exemplary embodiment will emerge as described below and with reference to the drawing. The examples listed do not represent a restriction of the invention.

DESCRIPTION OF PREFERRED EXEMPLARY EMBODIMENTS

Figure 1:
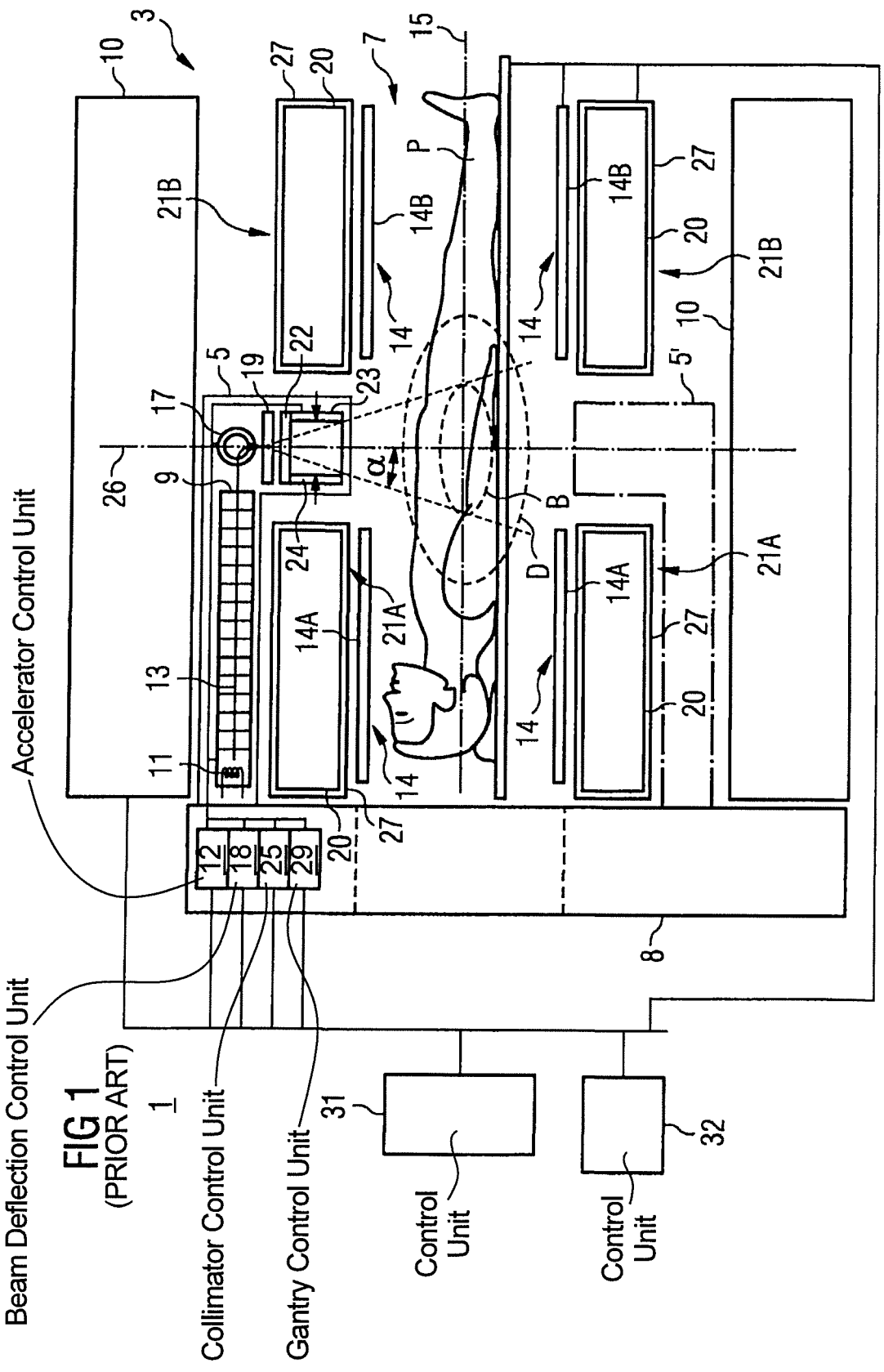
FIG. 1 is a schematic representation of a combined radiation therapy and magnetic resonance unit.
Figure 2:
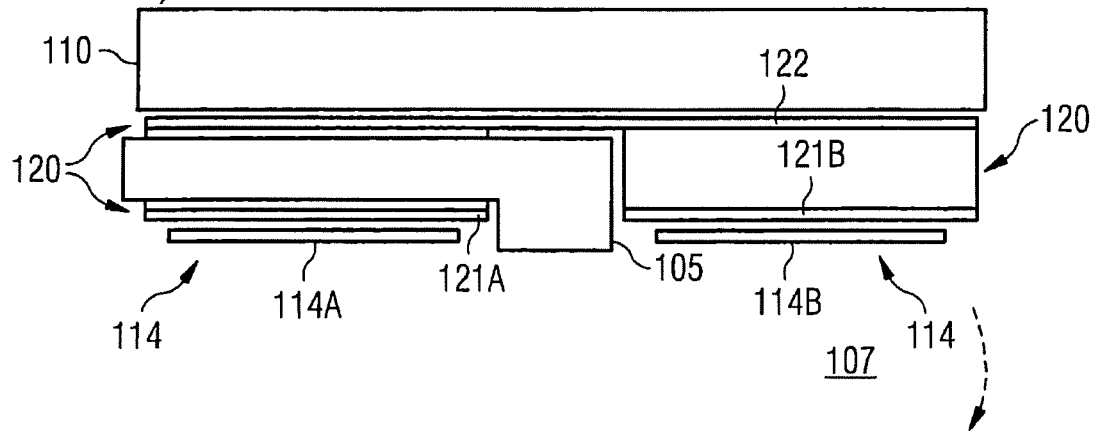
FIGS. 2-4 are schematic representations of segments of further configurations of a combined radiation therapy and magnetic resonance unit.
Figure 3:
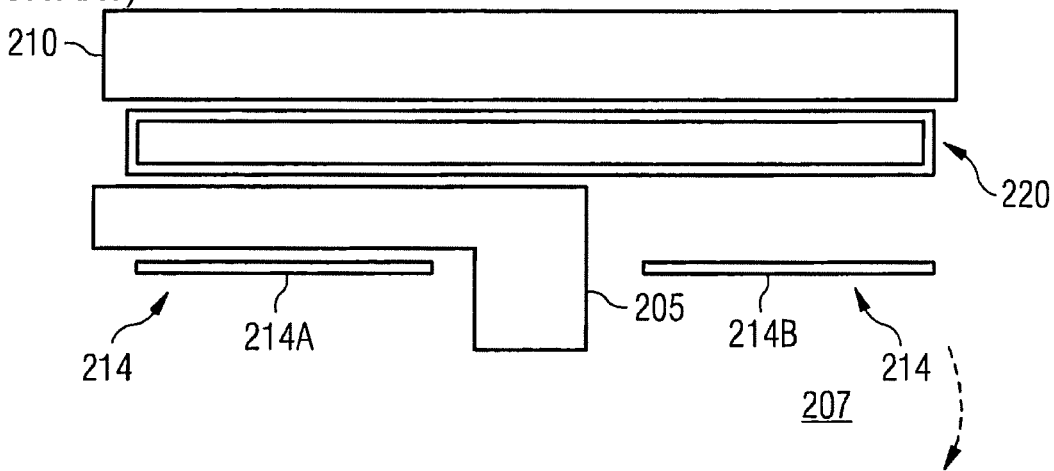
Figure 4:
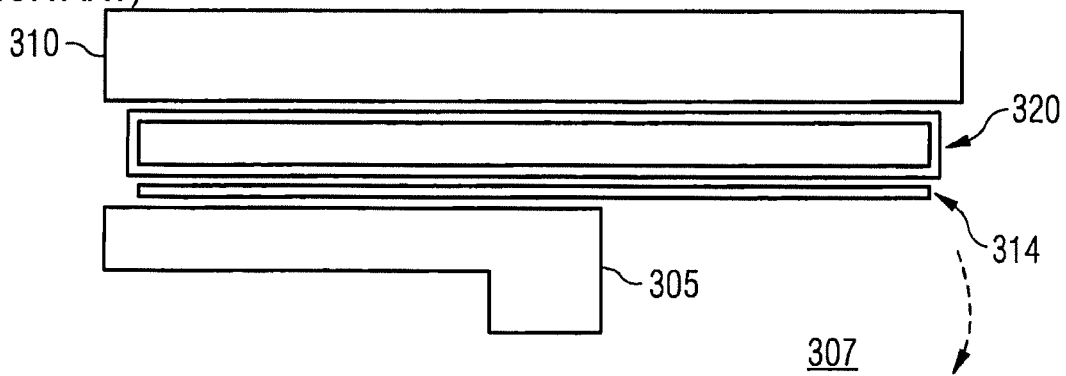

For the purposes of promoting an understanding of the principles of the invention, reference will now be made to preferred exemplary embodiments/best mode illustrated in the drawings and specific language will be used to describe the same. It will nevertheless be understood that no limitation of the scope of the invention is thereby intended, and such alterations and further modifications in the illustrated embodiments and such further applications of the principles of the invention as illustrated as would normally occur to one skilled in the art to which the invention relates are included herein.

FIGS. 5 to 8 show three examples of possible configurations of beam deflection arrangements 17 which can be used in a radiation therapy part of a combined radiation therapy and magnetic resonance unit, for example as described above.

The present exemplary embodiments provide beam deflection arrangements in which the electron beam is not subjected to the magnetic field of the main magnet as its path is deflected.

According to the present exemplary embodiments, this is achieved by applying a cancelling field, in the opposite direction to the main magnet field, so that the effective magnetic field in the region of the electron beam deflection is approximately zero, and further applying a deflecting magnetic field to cause the required deflection of the electron beam.

A stream of electrons moving through a magnetic field is subjected to a force which will deflect the path of the electrons. US 2008/0208036 describes various arrangements of beam deflection arrangement in which the electron beam is exposed to the main magnet field as well as to a further magnetic field applied for the purpose of deflecting the electron beam. This causes the electron beam to be deflected in a complex path, akin to a conical spiral. Modelling of such a path is difficult, and construction of deflection arrangements to achieve such a path is also difficult.

According to the preferred embodiments, by cancelling the main magnet background field in the region of the deflection path of the electron beam, the electron beam may follow a simpler deflection trajectory, in two-dimensions only. Such a deflection path is more easily modelled, and the arrangement to effect such a deflection is simpler to produce.

Figure 5:
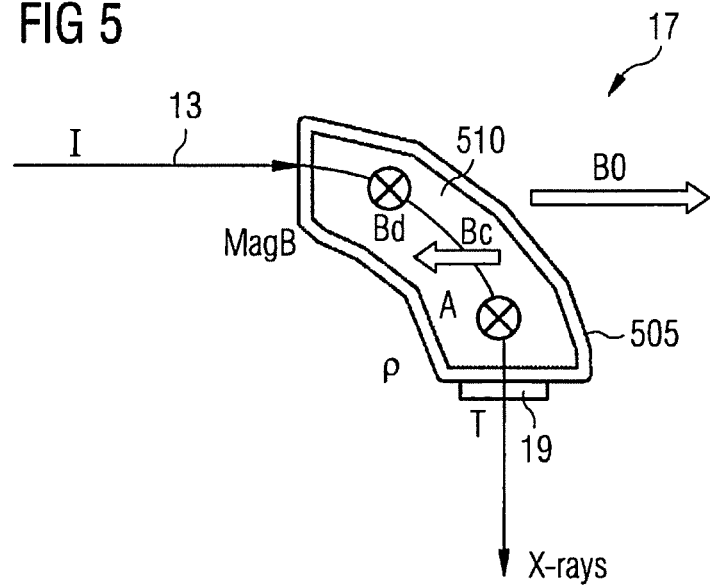
FIGS. 5-8 are exemplary configurations of beam deflection arrangements which can be used in a combined radiation therapy and magnetic resonance unit, in accordance with the exemplary embodiments.

FIG. 5 illustrates the concept of a first embodiment of the present invention.

As shown, the electron beam 13 is initially travelling in a direction parallel to the main magnet field B0. As such, the path of the electron beam is not affected by the main magnet field. A magnetic arrangement 505 causes deflection of the path of the electron beam, such that it hits target anode 19 to cause emission of X-rays.

According to this embodiment of the invention, magnetic arrangement or enclosure 505 encloses a volume 510 within which cancelling field $B_c$ is generated. Cancelling field Bc is essentially of equal magnitude to the main magnet field $B_0$ in the volume 510, but directed in the opposite direction. The overall effect is that fields $B_0$ and $B_c$ cancel each other out, leaving volume 510 essentially free of background field. Magnetic arrangement 505 also generates a deflection field $B_d$, directed perpendicular to the direction of travel of the electron beam. This deflection field has the effect of deflecting the electron beam 13 through an angle of 90°, in a plane, onto target 19. Magnetic arrangement 505 preferably extends to target 19, to prevent exposure of the electron beam 13 to the background field $B_0$ while the electron beam is travelling perpendicular to the main magnet field. If the electron beam were exposed to the main magnet field in that region, the beam would be deflected away from the target. The deflection field $B_d$ is represented in conventional notation as being directed away from the viewer in FIG. 5, and is preferably of constant intensity throughout the volume 510, leading the electron beam to follow an arc of radius ρ. The electron beam is deflected through 90°, and its momentum in the original direction of travel has become zero by the time it hits the target 19.

Figure 6:
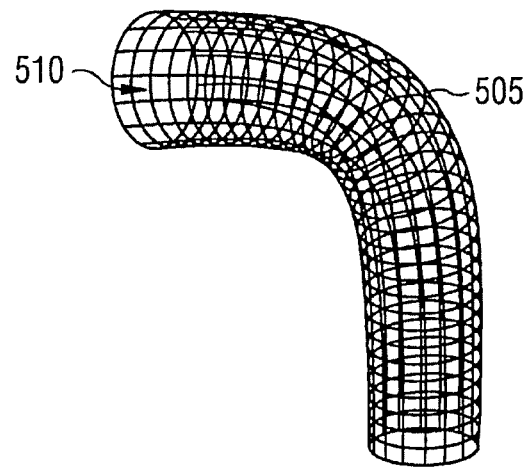

FIG. 6 shows a wire-frame representation of the shape of magnetic arrangement 505 and the enclosed volume 510 in an example embodiment.

Figure 7:
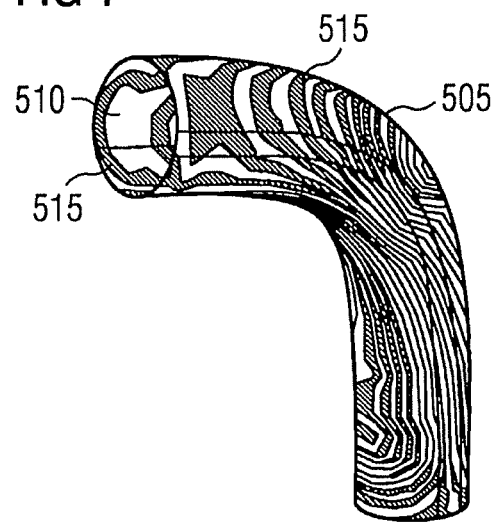

FIG. 7 shows a possible electrical arrangement of conductors, on the surface of a magnetic arrangement 505 of the shape illustrated in FIG. 6. The conductors 515 as shown have been positioned as calculated by a computer simulation to produce a combined magnetic field equal to the sum of the cancellation field $B_c$ and the deflection field $B_d$. As will be appreciated by those skilled in the art, the required arrangement of conductors 515 will vary according to several factors, including the required radius of deflection ρ, the energy of the incoming electron beam 13 and the strength of the main magnet field $B_0$.

Figure 8:
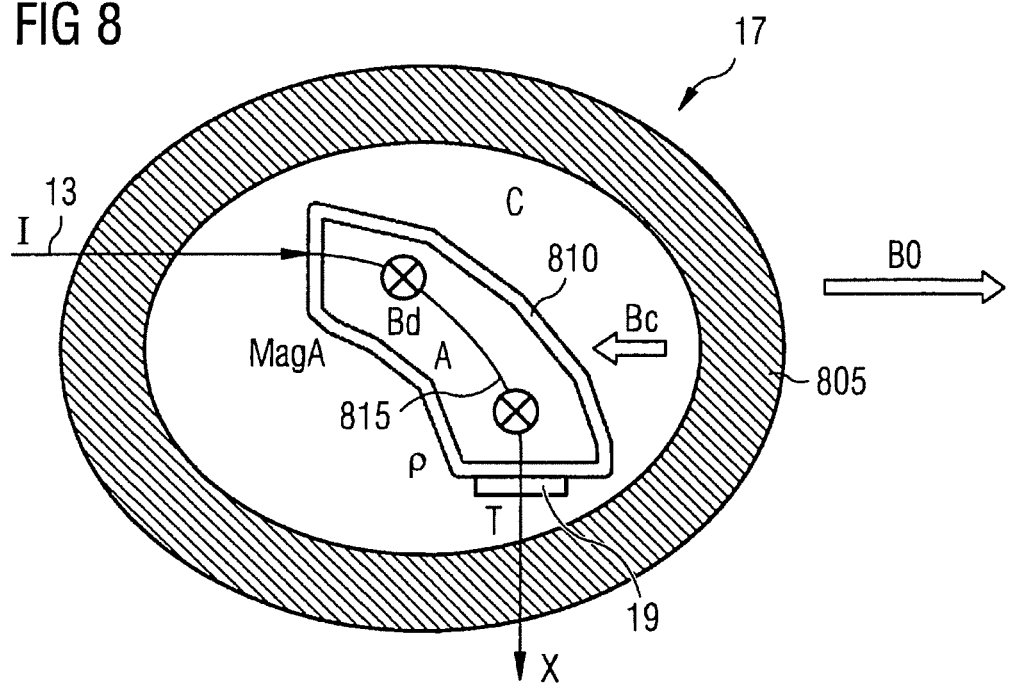

FIG. 8 shows a deflection arrangement 17 according to another embodiment of the present invention. According to this invention, a separate field cancelling magnet 805 is provided. This may comprise an electromagnet, such as a pair of coils arranged to generate a magnetic field $B_c$ of equal magnitude, but opposite direction, to the main magnet field $B_0$ in the region of the deflection of the electron beam 13. However, it may be preferred to use a permanent magnet arrangement to generate $B_c$, provided that it does not cause loss of homogeneity in an imaging region of the main magnet.

With the main magnet field $B_0$ effectively cancelled in the region of the beam deflection, the magnetic arrangement 810 need only deflect the electron beam as if in a zero background magnetic field.

In the arrangement of FIG. 8, a magnetic arrangement 810 of similar shape to the magnetic arrangement 505 of FIGS. 6-7 is provided, enclosing a volume 815. It only provides deflection field $B_d$. As with the arrangement of FIGS. 6-7, magnetic arrangement 810 generates a deflection field $B_d$, directed perpendicular to the direction of travel of the electron beam 13. This deflection field has the effect of deflecting the electron beam through an angle of 90°, in a plane, onto target 19. The electron beam's momentum in the original direction of travel has become zero by the time it hits the target 19.

Magnetic arrangement 810 preferably extends to target 19, to prevent exposure of the electron beam 13 to the background field $B_0$ while the electron beam is travelling perpendicular to the main magnet field. If the electron beam were exposed to the main magnet field in that region, the beam would be deflected way from the target. The deflection field $B_d$ is represented in conventional notation as being directed away from the viewer in FIG. 8, and is preferably of constant intensity throughout the volume 815, leading the electron beam to follow an arc of radius ρ.

Computer simulations, well within the capability of those skilled in the art, may be performed to determine an appropriate pattern of conductors, and an appropriate DC current, to apply to the magnetic arrangement 810. The magnetic arrangement must provide the required deviation for the electron beam, yet not provide a stray field so strong that it interferes with the homogeneity of the main magnet field.

Depending on the chosen operation of the radiation therapy part, the magnetic arrangements 505, 810, 805 may be operated intermittently, as a pulsed magnet.

Although preferred exemplary embodiments are shown and described in detail in the drawings and in the preceding specification, they should be viewed as purely exemplary and not as limiting the invention. It is noted that only preferred exemplary embodiments are shown and described, and all variations and modifications that presently or in the future lie within the protective scope of the invention should be protected.

The invention claimed is:

1. A combined radiation therapy and magnetic resonance unit, comprising:
   a magnetic resonance diagnosis part with an interior within which a main magnet generates a main magnet field, said interior being limited in a radial direction about an axis by the main magnet, and a radiation therapy part for irradiation of an irradiation area within the interior, said radiation therapy part comprising an electron beam accelerator which provides an electron beam directed parallel to the main magnet field;

at least parts of the radiation therapy part comprising a beam deflection enclosure defining an enclosed volume entirely radially surrounding the electron beam and deflecting the electron beam in a single plane and along a two dimensional trajectory lying within said plane and toward the axis from an initial trajectory parallel to the axis, said enclosure being arranged within the interior; and said beam deflection enclosure comprising a magnetic arrangement creating first and second magnetic fields, the first magnetic field being of magnitude equal to a magnitude of the main magnet field in a region of the beam deflection enclosure, but of opposite direction, and effective to cancel the main magnet field in the region of the beam deflection enclosure, and the second magnetic field in the region of the beam deflection enclosure and directed perpendicular to said two dimensional trajectory of the electron beam throughout said two dimensional trajectory to cause the electron beam to be deflected inward into the interior and towards the axis.

2. The combined radiation therapy and magnetic resonance unit as claimed in claim 1 wherein the beam deflection enclosure is configured to deflect the electron beam through 90° radially inward.

3. The combined radiation therapy and magnetic resonance unit as claimed in claim 1 wherein the beam deflection enclosure comprises at least one electromagnet.

4. The combined radiation therapy and magnetic resonance unit as claimed in claim 1 wherein the beam deflection enclosure comprises at least one permanent magnet.

5. The combined radiation therapy and magnetic resonance unit as claimed in claim 1 wherein the beam deflection enclosure comprises at least one pulsed magnet.

6. The combined radiation therapy and magnetic resonance unit as claimed in claim 1 wherein the first magnetic field is generated within the enclosed volume.

7. The combined radiation therapy and magnetic resonance unit as claimed in claim 6 wherein the beam deflection enclosure is tubular, and shaped to contain an arcuate path of the electron beam as it is deflected towards the axis.

8. The combined radiation therapy and magnetic resonance unit as claimed in claim 7 wherein the beam deflection enclosure carries conductors in such a pattern that a DC current flowing through the conductors generates the first magnetic field and the second magnetic field.

9. The combined radiation therapy and magnetic resonance unit as claimed in claim 1 wherein the beam deflection enclosure is tubular, and shaped to contain an arcuate path of the electron beam as it is deflected towards the axis.

10. The combined radiation therapy and magnetic resonance unit as claimed in claim 9 wherein the beam deflection enclosure carries conductors in such a pattern that a DC current flowing through the conductors generates the second magnetic field.

* * * * *